United States Patent
Inoue et al.

(10) Patent No.: US 6,514,902 B1
(45) Date of Patent: Feb. 4, 2003

(54) METHOD FOR PRODUCING AN OXIDE CATALYST FOR USE IN PRODUCING ACRYLONITRILE OR METHACRYLONITRILE FROM PROPANE OR ISOBUTANE

(75) Inventors: Tomoya Inoue, Kurashiki (JP); Hiroshi Ishida, Kurashiki (JP)

(73) Assignee: Asahi Kasei Kogyo Kabushiki Kaisha, Osaka (JP)

( * ) Notice: Subject to any disclaimer, the term of this patent is extended or adjusted under 35 U.S.C. 154(b) by 0 days.

(21) Appl. No.: 09/674,736

(22) PCT Filed: Aug. 30, 1999

(86) PCT No.: PCT/JP99/04686

§ 371 (c)(1),
(2), (4) Date: Nov. 3, 2000

(87) PCT Pub. No.: WO00/12209

PCT Pub. Date: Mar. 9, 2000

(30) Foreign Application Priority Data

Aug. 28, 1998 (JP) .......................... 10-243739
Sep. 22, 1998 (JP) .......................... 10-267958

(51) Int. Cl.$^7$ ............................. B01J 23/00
(52) U.S. Cl. ............. 502/305; 502/306; 502/307; 502/308; 502/309; 502/310; 502/311; 502/312; 502/313; 502/314; 502/315; 502/316; 502/317; 502/319; 502/320; 502/321; 502/322; 502/323; 558/319
(58) Field of Search .................. 502/305, 306, 502/307, 308, 309, 310, 311, 312, 313, 314, 315, 316, 317, 318, 319, 320, 321, 322, 323, 113, 104; 558/319

(56) References Cited

U.S. PATENT DOCUMENTS

| | | | | | |
|---|---|---|---|---|---|
| RE28,593 E | * | 10/1975 | Bethell et al. | .......... | 260/530 N |
| 4,051,180 A | * | 9/1977 | Shaw et al. | .......... | 260/530 N |
| 4,082,698 A | * | 4/1978 | Shaw et al. | .......... | 252/469 |
| 4,305,843 A | * | 12/1981 | Krabetz et al. | .......... | 252/432 |
| 4,330,429 A | * | 5/1982 | Sasaki et al. | .......... | 252/413 |
| 4,374,758 A | * | 2/1983 | Sasaki et al. | .......... | 252/439 |
| 4,378,309 A | * | 3/1983 | Shaw et al. | .......... | 252/469 |
| 4,524,236 A | * | 6/1985 | McCain | .......... | 585/658 |
| 4,568,790 A | * | 2/1986 | McCain | .......... | 585/658 |
| 4,596,787 A | * | 6/1986 | Manyik et al. | .......... | 502/312 |
| 4,826,802 A | * | 5/1989 | Sasaki et al. | .......... | 502/206 |
| 4,892,856 A | * | 1/1990 | Kawajiri et al. | .......... | 502/247 |
| 5,049,692 A | * | 9/1991 | Hatano et al. | .......... | 558/319 |
| 5,094,989 A | | 3/1992 | Lynch et al. | | |
| 5,102,846 A | * | 4/1992 | Kuroda et al. | .......... | 502/205 |
| 5,102,847 A | * | 4/1992 | Yamamoto et al. | .......... | 502/209 |
| 5,173,468 A | * | 12/1992 | Boehning et al. | .......... | 502/209 |
| 5,206,201 A | * | 4/1993 | Kishimoto et al. | .......... | 502/206 |
| 5,231,214 A | * | 7/1993 | Ushikubo et al. | .......... | 558/319 |
| 5,472,925 A | * | 12/1995 | Ushikubo et al. | .......... | 502/312 |
| 5,681,790 A | * | 10/1997 | Kim et al. | .......... | 502/164 |
| 5,821,192 A | * | 10/1998 | Seely et al. | .......... | 502/353 |
| 5,959,143 A | * | 9/1999 | Sugi et al. | .......... | 562/534 |
| 5,973,186 A | * | 10/1999 | Midorikawa et al. | .......... | 558/319 |
| 6,013,597 A | * | 1/2000 | Karim et al. | .......... | 502/209 |
| 6,030,920 A | * | 2/2000 | Karim et al. | .......... | 502/312 |
| 6,080,882 A | * | 6/2000 | Midorikawa et al. | .......... | 558/319 |

FOREIGN PATENT DOCUMENTS

| | | |
|---|---|---|
| EP | 0389701 | 1/1990 |
| JP | 57075147 | 5/1982 |
| JP | 11226048 | 8/1998 |

* cited by examiner

*Primary Examiner*—Stanley S. Silverman
*Assistant Examiner*—Cam N. Nguyen
(74) *Attorney, Agent, or Firm*—Pennie & Edmonds LLP

(57) ABSTRACT

Disclosed is a process for producing an oxide catalyst for use in producing (meth)acrylonitrile from propane or isobutane by ammoxidation in the gaseous phase, the oxide catalyst comprising a compound oxide containing Mo, V and Sb as essential component elements, which process comprises subjecting a solution or slurry, in water and/or an alcohol, of a raw-material mixture comprising a Mo compound, a V compound and an Sb compound as essential raw materials to a specific oxidation treatment using an oxidizing gas and/or an oxidizing liquid before subjecting the solution or slurry to drying and subsequent calcination. Further, also disclosed is a process for producing a base-treated oxide catalyst by treating the above-mentioned oxide catalyst with an aqueous basic solution.

14 Claims, No Drawings

METHOD FOR PRODUCING AN OXIDE CATALYST FOR USE IN PRODUCING ACRYLONITRILE OR METHACRYLONITRILE FROM PROPANE OR ISOBUTANE

BACKGROUND OF THE INVENTION

1. Field of the Invention

The present invention relates to a process for producing an oxide catalyst for use in producing acrylonitrile or methacrylonitrile from propane or isobutane. More particularly, the present invention is concerned with a process for producing an oxide catalyst for use in producing acrylonitrile or methacrylonitrile from propane or isobutane by ammoxidation in the gaseous phase, wherein the oxide catalyst comprises a compound oxide containing molybdenum (Mo), vanadium (V), antimony (Sb) and optionally an element X. The process comprises subjecting a solution or slurry, in water and/or an alcohol, of a raw material mixture comprising a Mo compound, a V compound, an Sb compound and optionally an X compound to a specific oxidation treatment using an oxidizing gas and/or an oxidizing liquid before subjecting the raw material mixture solution or slurry to drying and subsequent calcination. When the oxide catalyst produced by the process of the present invention is used in the production of acrylonitrile or methacrylonitrile, not only can the desired acrylonitrile or methacrylonitrile be produced in high yield and in high space time yield, but also the deterioration of the catalyst is suppressed, so that production of acrylonitrile or methacrylonitrile can be stably performed for a prolonged period of time.

2. Prior Art

Recently, attention has been attracted to a technique for producing acrylonitrile or methacrylonitrile by a gaseous-phase catalytic ammoxidation of propane or isobutane, as a substitute for a gaseous-phase catalytic ammoxidation of propylene or isobutylene, and a number of proposals have been made with respect to a catalyst for use in the ammoxidation of propane or isobutane.

For example, as a catalyst for use in the ammoxidation of propane or isobutane, a compound oxide catalyst containing molybdenum (Mo), vanadium (V), tellurium (Te) and niobium (Nb) is known. Such a compound oxide catalyst is disclosed in, for example, Unexamined Japanese Patent Application Laid-Open Specification Nos. 2-257 (corresponding to U.S. Pat. No. 5,049,692), 5-148212 (corresponding to U.S. Pat. No. 5,231,214), 5-208136 (corresponding to European Patent No. 529,853), 6-227819, 6-285372 (corresponding to U.S. Pat. No. 5,422,328), 7-144132, 7-232071, 8-57319 and 8-141401.

When the above-mentioned catalyst is used for the ammoxidation of propane or isobutane, the yield and space time yield of acrylonitrile or methacrylonitrile {hereinafter, frequently referred to as "(meth)acrylonitrile")} become high. However, this catalyst has a problem in that during the production of the (meth)acrylonitrile, the tellurium is volatilized from the catalyst, thereby leading to a deterioration of the catalyst.

For this reason, as described below, oxide catalysts containing Mo, V and antimony (Sb) and oxide catalysts containing Mo, V, Sb and Nb, each of which contains antimony in place of tellurium which is likely to be volatilized from a catalyst, have been proposed.

For example, a compound oxide catalyst containing Mo, V, Sb and Nb (wherein Nb is an optional component) is disclosed in Unexamined Japanese Patent Application Laid-Open Specification Nos. 9-157241 (corresponding to U.S. Pat. No. 5,750,760) and 10-28862. This catalyst is produced using an aqueous solution containing a molybdenum compound, a vanadium compound, an antimony compound and optionally a niobium compound. The catalyst production process described in those documents comprises mixing a compound of pentavalent vanadium and a compound of trivalent antimony so as to reduce the vanadium, or mixing a compound of hexavalent molybdenum and a compound of trivalent antimony so as to reduce the molybdenum; mixing the resultant reaction mixture with compounds of other component elements to thereby obtain a mixture; and drying the obtained mixture, followed by calcination. Specifically, in these documents, the oxide catalyst is produced by a process comprising heat-aging an aqueous slurry containing a compound of pentavalent vanadium and a compound of trivalent antimony, followed by addition of a molybdenum compound and a niobium compound, thereby obtaining an aqueous mixture; optionally cooling the obtained aqueous mixture; and drying the aqueous mixture, followed by calcination.

When the catalyst produced by the above-mentioned process is used for the production of (meth)acrylonitrile, the desired (meth)acrylonitrile can be produced in a relatively high yield. However, the space time yield of (meth)acrylonitrile [molar amount of (meth)acrylonitrile formed ($\mu$mol)/time of contact (contact time) between the raw material and the catalyst (g·sec/ml)×catalyst weight (g)] is disadvantageously as low as 0.11 to 0.22 [($\mu$mol/{(g·sec/ml)·g}]. Therefore, the productivity of (meth)acrylonitrile per reactor becomes low. Further, when it is attempted to improve the space time yield of (meth)acrylonitrile by employing a high reaction temperature, the selectivity for (meth)acrylonitrile is lowered, so that the yield of (meth)acrylonitrile also is lowered.

Unexamined Japanese Patent Application Laid-Open Specification No. 5-293374 (corresponding to U.S. Pat. No. 5,094,989) describes an oxide catalyst which contains V and Sb as major components, and also contains a small amount of Mo. However, when this catalyst is used in the production of (meth)acrylonitrile, not only is a high reaction temperature needed, but also the yield of (meth)acrylonitrile is low.

New Developments in Selective Oxidation pp. 515–525 (1990) reports the results of the ammoxidation of propane which was performed using a catalyst comprising alumina having supported thereon a compound oxide containing Mo, V and Sb in a molar ratio of 1/0.14/0.71. According to this document, the above-mentioned catalyst has a problem in that not only the selectivity for (meth)acrylonitrile but also the activity to perform the desired conversion are low.

U.S. Pat. No. 4,760,159 describes an oxide catalyst which contains bismuth, vanadium and antimony as major components, and also contains a small amount of molybdenum. However, when this catalyst is used in the production of (meth)acrylonitrile a problem arises not only in that a high reaction temperature is needed, but also in that the yield of (meth)acrylonitrile is low.

As is apparent from the above, with respect to the oxide catalyst comprising Mo—V—Sb or Mo—V—Sb—Nb, the deterioration thereof during the production of (meth)acrylonitrile is suppressed, but not only the conversion-selectivity-based yield (hereinafter referred to simply as "yield") but also the space time yield of (meth)acrylonitrile is low.

Further, the oxide catalyst comprising Mo—V—Sb or Mo—V—Sb—Nb has the following problem. As described in *Applied Catalysis A General*, Vol. 157, 143–172 (1997), in the ammoxidation of propane, ammonia is converted to not only acrylonitrile (the desired compound of the ammoxidation) but also to various by-products, such as acetonitrile and hydrocyanic acid as well as nitrogen (an oxidative decomposition product). When the oxide catalyst comprising Mo—V—Sb or Mo—V—Sb—Nb is used for the ammoxidation, the decomposition of ammonia into nitrogen vigorously occurs (that is, the ratio of ammonia decomposed to form nitrogen is high), so that the loss of ammonia is large.

SUMMARY OF THE INVENTION

In this situation, the present inventors have made extensive and intensive studies to solve the above-mentioned problems accompanying the prior art. As a result, it has unexpectedly been found that, in the production of an oxide catalyst comprising a compound oxide containing at least molybdenum (Mo), vanadium (V) and antimony (Sb), when a solution or slurry, in water and/or an alcohol, of a raw material mixture comprising at least an Mo compound, a V compound and an Sb compound is subjected to a specific oxidation treatment, and the resultant oxidized raw material mixture solution or slurry is then dried to thereby obtain a dried catalyst precursor, followed by calcination of the dried catalyst precursor, an oxide catalyst can be obtained which is not only insusceptible to deterioration during the production of (meth)acrylonitrile (that is, unlikely to be deactivated), but also effective for producing (meth)acrylonitrile in high yield and high space time yield, and which, therefore, can be advantageously used for effectively, efficiently producing (meth)acrylonitrile for a prolonged period of time.

Further, it has also unexpectedly been found that, when a base-treated oxide catalyst, which can be obtained by treating the above-mentioned oxide catalyst with an aqueous basic solution, is used in the production of acrylonitrile or methacrylonitrile from propane or isobutane by ammoxidation in the gaseous phase, not only can the above-mentioned excellent effects be achieved, but also it becomes possible to suppress the decomposition of ammonia, which is one of the materials for the production of acrylonitrile or methacrylonitrile, into nitrogen, so that the utility of the ammonia can be remarkably enhanced.

The present invention has been completed, based on the above novel findings.

Accordingly, it is a primary object of the present invention to provide a process for producing an excellent oxide-catalyst which is not only insusceptible to deterioration during the production of acrylonitrile or methacrylonitrile, but also effective for stably producing acrylonitrile or methacrylonitrile in high yield and high space time yield, and which, therefore, can be advantageously used for stably conducting an efficient production of acrylonitrile or methacrylonitrile for a prolonged period of time.

It is another object of the present invention to provide a process for producing a base-treated oxide catalyst by treating the above-mentioned oxide catalyst with an aqueous basic solution, wherein the base-treated catalyst not only has the above-mentioned excellent effects, but also is capable of suppressing the decomposition of ammonia, which is one of the materials for the production of acrylonitrile or methacrylonitrile, into nitrogen, so that the utility of the ammonia can be remarkably enhanced.

The foregoing and other objects, and advantages of the present invention will be apparent to those skilled in the art-from the following detailed description taken in connection with the appended claims.

DETAILED DESCRIPTION OF THE INVENTION

In a primary aspect of the present invention, there is provided a process for producing an oxide catalyst for use in producing acrylonitrile or methacrylonitrile from propane or isobutane by ammoxidation in the gaseous phase, the oxide catalyst comprising a compound oxide represented by the following formula:

$$Mo_{0.1}V_aSb_bX_cO_n \qquad (I)$$

wherein:
X represents at least one element selected from the group consisting of niobium, tungsten, chromium, titanium, tantalum, zirconium, hafnium, manganese, rhenium, iron, ruthenium, cobalt, rhodium, nickel, palladium, platinum, copper, silver, zinc, boron, gallium, indium, germanium, tin, tellurium, phosphorus, lead, bismuth, rare earth elements, and alkaline earth metals; and a, b, c and n are, respectively, the atomic ratios of vanadium (V), antimony (Sb), X and oxygen (O), relative to molybdenum (Mo),
wherein
$0.1 \leq a \leq 1.0$,
$0.01 \leq b \leq 0.6$,
$0 \leq c \leq 1.0$, and
n is a number determined by and consistent with the valence requirements of the other elements present in the compound oxide of formula (I), which comprises the following steps (1) to (5):

(1) providing a solution or slurry of a raw material mixture in at least one liquid medium selected from the group consisting of water and an alcohol, the raw material mixture comprising a molybdenum (Mo) compound, a vanadium (V) compound, an antimony (Sb) compound and optionally at least one X compound selected from the group consisting of compounds of elements defined as X in formula (I), (2) subjecting the raw material mixture solution or slurry to at least one oxidation treatment selected from the group consisting of:
(2-a) a heat treatment at 50 to 300° C. in the presence of an oxidizing gas for 1 hour or more, and
(2-b) a treatment with an oxidizing liquid, thereby obtaining an oxidized raw material mixture solution or slurry, (3) optionally adding to the oxidized raw material mixture solution or slurry obtained in step (2) at least one X compound selected from the group consisting of compounds of elements defined as X in formula (I), (4) drying the oxidized raw material mixture solution or slurry obtained in step (2) or the oxidized raw material mixture solution or slurry having added thereto the X compound obtained in step (3), to thereby obtain a dried catalyst precursor, and (5) calcining the dried catalyst precursor to thereby obtain an oxide catalyst comprising a compound oxide of formula (I).

For an easy understanding of the present invention, the essential features and various preferred embodiments of the present invention are enumerated below.

1. A process for producing an oxide catalyst for use in producing acrylonitrile or methacrylonitrile from propane or isobutane by ammoxidation in the gaseous phase, the oxide catalyst comprising a compound oxide represented by the following formula:

$$Mo_{0.1}V_aSb_bX_cO_n \quad (I)$$

wherein:
X represents at least one element selected from the group consisting of niobium, tungsten, chromium, titanium, tantalum, zirconium, hafnium, manganese, rhenium, iron, ruthenium, cobalt, rhodium, nickel, palladium, platinum, copper, silver, zinc, boron, gallium, indium, germanium, tin, tellurium, phosphorus, lead, bismuth, rare earth elements, and alkaline earth metals; and
a, b, c and n are, respectively, the atomic ratios of vanadium (V), antimony (Sb), X and oxygen (O), relative to molybdenum (Mo),
wherein
$0.1 \leq a \leq 1.0$,
$0.01 \leq b \leq 0.6$,
$0 \leq c \leq 1.0$, and
n is a number determined by and consistent with the valence requirements of the other elements present in the compound oxide of formula (I), which comprises the following steps (1) to (5):
(1) providing a solution or slurry of a raw material mixture in at least one liquid medium selected from the group consisting of water and an alcohol, the raw material mixture comprising a molybdenum (Mo) compound, a vanadium (V) compound, an antimony (Sb) compound and optionally at least one X compound selected from the group consisting of compounds of elements defined as X in formula (I),
(2) subjecting the raw material mixture solution or slurry to at least one oxidation treatment selected from the group consisting of:
(2-a) a heat treatment at 50 to 300° C. in the presence of an oxidizing gas for 1 hour or more, and
(2-b) a treatment with an oxidizing liquid, thereby obtaining an oxidized raw material mixture solution or slurry,
(3) optionally adding to the oxidized raw material mixture solution or slurry obtained in step (2) at least one X compound selected from the group consisting of compounds of elements defined as X in formula (I),
(4) drying the oxidized raw material mixture solution or slurry obtained in step (2) or the oxidized raw material mixture solution or slurry having added thereto the X compound obtained in step (3), to thereby obtain a dried catalyst precursor; and
(5) calcining the dried catalyst precursor to thereby obtain an oxide catalyst comprising a compound oxide of formula (I).

2. The process according to item 1 above, wherein the oxidizing gas is at least one member selected from the group consisting of oxygen, air and nitrogen oxides.

3. The process according to item 1 or 2 above, wherein the oxidizing liquid is an aqueous solution of at least one oxidizer compound selected from the group consisting of hydrogen peroxide, nitric acid and hypochlorous acid.

4. The process according to item 3 above, wherein the amount of the oxidizing liquid is in the range of from 0.01 to 2 in terms of the molar ratio of the at least one oxidizer compound to the antimony contained in the raw material mixture solution or slurry provided in step (1).

5. The process according to item 3 or 4 above, wherein the oxidizing liquid is an aqueous solution of hydrogen peroxide.

6. The process according to any one of items 1 to 5 above, wherein the calcination in step (5) is performed in an inert gas atmosphere which is substantially free from molecular oxygen.

7. The process according to any one of items 1 to 6 above, wherein the calcination in step (5) is performed at 400 to 700° C.

8. The process according to any one of items 1 to 7 above, which further comprises the steps of (6) contacting the oxide catalyst obtained in step (5) with an aqueous basic solution to obtain a contact mixture containing a base-treated oxide catalyst, and (7) separating and recovering the base-treated oxide catalyst from the contact mixture.

9. The process according to item 8 above, wherein the aqueous basic solution is an aqueous solution of at least one compound selected from the group consisting of ammonia, an alkali metal hydroxide, an alkaline earth metal hydroxide, an alkali metal carbonate, an alkaline earth metal carbonate, an alkali metal salt of an organic acid, an alkaline earth metal salt of an organic acid and an amine.

10. The process according to item 9 above, wherein the aqueous basic solution is an aqueous solution of ammonia.

11. The process according to any one of items 8 to 10 above, which further comprises the step (8) of calcining the base-treated oxide catalyst recovered in step (7) from the contact mixture.

12. The process according to item 11 above, wherein the calcination in step (8) is performed in an inert gas atmosphere which is substantially free from molecular oxygen.

13. The process according to item 11 or 12 above, wherein the calcination in step (8) is performed at 400 to 700° C.

14. An oxide catalyst for use in producing acrylonitrile or methacrylonitrile from propane or isobutane by ammoxidation in the gaseous phase, which is substantially the same as that produced by the process of any one of items 1 to 13 above.

15. A process for producing acrylonitrile or methacrylonitrile, which comprises reacting propane or isobutane with ammonia and molecular oxygen in the gaseous phase in the presence of the oxide catalyst of item 14 above.

Hereinbelow, the present invention will be described in more detail.

The compound oxide of the oxide catalyst produced by the process of the present invention has a composition represented by the following formula (I):

$$M_{0.1}V_aSb_bX_cO_n \quad (I)$$

wherein:
X represents at least one element selected from the group consisting of niobium, tungsten, chromium, titanium, tantalum, zirconium, hafnium, manganese, rhenium, iron, ruthenium, cobalt, rhodium, nickel, palladium, platinum, copper, silver, zinc, boron, gallium, indium, germanium, tin, tellurium, phosphorus, lead, bismuth, rare earth elements, and alkaline earth metals; and
a, b, c and n are, respectively, the atomic ratios of vanadium (V), antimony (Sb), X and oxygen (O), relative to molybdenum (Mo),
wherein
$0.1 \leq a \leq 1.0$,
$0.01 \leq b \leq 0.6$,
$0 \leq c \leq 1.0$, and n is a number determined by and consistent with the valence requirements of the other elements present in the compound oxide of formula (I).

As element X in formula (I) above, preferred are niobium (Nb), tungsten (W), tin (Sn) and titanium (Ti), and especially preferred are Nb and Ti. It is preferred that the atomic ratio (a) of vanadium (V) to Mo satisfies the relationship: $0.1 \leq a \leq 0.5$, more preferably $0.2 \leq a \leq 0.4$. It is preferred that the atomic ratio (b) of antimony (Sb) to Mo satisfies the relationship: $0.1 \leq b \leq 0.3$, more preferably $0.1 \leq b \leq 0.25$. It is preferred that the atomic ratio (c) of X to Mo satisfies the relationship: $0.01 \leq c \leq 0.5$, more preferably $0.01 \leq c \leq 0.2$, with the proviso that, when the above-mentioned compound oxide contains tellurium (Te) as element X, it is preferred that the atomic ratio (c') of Te to Mo generally satisfies the relationship: $0.001 \leq c' \leq 0.07$, preferably $0.001 \leq c' \leq 0.03$, especially preferably $0.001 \leq c' \leq 0.01$.

Conventionally, an oxide catalyst containing Mo, V and Sb is produced by a process comprising:

preparing a solution or slurry of a raw material mixture comprising a molybdenum (Mo) compound, a vanadium (V) compound and an antimony (Sb) compound;

drying the raw material mixture solution or slurry, thereby obtaining a dried catalyst precursor (drying step); and calcining the obtained dried catalyst precursor (calcination step).

In contrast, the essential feature of the process of the present invention resides in that, in the process for producing an oxide catalyst comprising a compound oxide represented by formula (I) above which contains at least Mo, V and Sb, a solution or slurry, in water and/or an alcohol, of a raw material mixture comprising at least an Mo compound, a V compound and an Sb compound is subjected to a specific oxidation treatment as described below prior to the drying step and the subsequent calcination step, thereby remarkably advancing the oxidation of the Mo, V and Sb. By virtue of such a characteristic feature of the process of the present invention, it has become possible to produce an oxide catalyst which is not only insusceptible to deterioration during the production of the (meth)acrylonitrile, but also useful for effectively, efficiently producing (meth)acrylonitrile in high yield and high space time yield.

As mentioned above, the process of the present invention comprises the following steps (1) to (5):

(1) providing a solution or slurry, in water and/or an alcohol, of a raw material mixture comprising a molybdenum compound, a vanadium compound, an antimony compound and optionally an X compound, (2) subjecting the raw material mixture solution or slurry to a specific oxidation treatment, thereby obtaining an oxidized raw material mixture solution or slurry, (3) optionally adding to the oxidized raw material mixture solution or slurry obtained in step (2) an X compound, (4) drying the oxidized raw material mixture solution or slurry obtained in step (2) or (3) which optionally contains the X compound, to thereby obtain a dried catalyst precursor, and (5) calcining the dried catalyst precursor to thereby obtain an oxide catalyst comprising a compound oxide of formula (I).

Hereinbelow, the steps involved in the process of the present invention will be described in more detail.

Step (1). Raw Material Mixture Preparation Step

In step (1) of the process of the present invention, a raw material mixture comprising a molybdenum compound, a vanadium compound, an antimony compound and optionally at least one X compound selected from the group consisting of compounds of elements defined as X in formula (I) is dissolved or dispersed in at least one liquid medium selected from the group consisting of water and an alcohol so as to provide a solution or slurry of the raw material mixture.

As a liquid medium, at least one medium selected from, the group consisting of water and an alcohol can be used. Examples of alcohols used in the present invention include $C_1$–$C_4$ alcohols and benzyl alcohol. With respect to the amount of the liquid medium, there is no particular limitation as long as the amount of the liquid medium is sufficient for forming a solution or slurry of the raw material mixture. However, from the viewpoint of the solubility of the respective raw material compounds of the component elements and the promotion of the reactions subsequently occurring in the liquid medium; it is preferred to use 4 to 20 g of the liquid medium per gram of the molybdenum compound in the raw material mixture. When a mixture of water and an alcohol is used as a liquid medium, the ratio of water to the alcohol is appropriately selected, taking into consideration the solubility of the compounds contained in the raw material mixture in water and the alcohol.

In the process of the present invention for producing an oxide catalyst comprising a compound oxide, the following compounds can be used as sources of the component elements of the oxide catalyst.

Examples of sources of molybdenum include ammonium heptamolybdate, molybdenum oxides, molybdenum oxychlorides, molybdenum alkoxides and the like. Of these, hexavalent molybdenum compounds, especially ammonium heptamolybdate is preferred.

Examples of sources of vanadium include ammonium metavanadate, vanadium (V) oxide, vanadium oxychlorides, vanadium alkoxides and the like. Of these, pentavalent vanadium compounds, especially ammonium metavanadate or vanadium (V) oxide is preferred.

Examples of sources of antimony include antimony (III) oxide, antimony (V) oxide, antimony chlorides, antimony (III) oxychloride, antimony (III) nitrate oxide, antimony alkoxides, and organic acid salts of antimony, such as antimony tartrate and the like. Of these, trivalent antimony compounds, especially antimony (III) oxide is preferred.

Examples of sources of X elements include dicarboxylic acid salts, hydroxides, oxides, nitrates, acetates, ammonium salts, carbonates and alkoxides of the X elements and the like. When niobium and/or titanium is used as the X element, an aqueous solution of a dicarboxylate thereof can be preferably used. With respect to the source of niobium, it is preferred to use a niobic acid. The "niobic acid" is a hydrated compound represented by the following formula: $Nb_2O_5 \cdot nH_2O$, which is also known as "niobium hydroxide" or "niobium oxide hydrate". It is especially preferred to use a niobium-containing aqueous solution disclosed in EP 0895809 A1, which comprises water having dissolved therein a dicarboxylic acid, a niobium compound and optionally ammonia, wherein the molar ratio of the dicarboxylic acid to niobium is in the range of from 1 to 4, and the ammonia/niobium molar ratio is 0 to 2. In the present invention, however, the molar ratio of the dicarboxylic acid to niobium can be more than 4, as long as the molar ratio is 10 or less. In the niobium-containing aqueous solution used in the present invention, the preferred molar ratio of the dicarboxylic acid to niobium is in the range of 2 to 6. As the above-mentioned dicarboxylic acid, preferred is oxalic acid.

The suitable amounts of the molybdenum compound, vanadium compound, antimony compound and X-element compound as a compound of an optional component element vary depending on the types of the compounds used, and the amounts are appropriately selected so that a compound oxide having the composition represented by formula (I) is obtained.

There is no particular limitation with respect to the method for preparing a raw material mixture solution or slurry by combining the above-mentioned liquid medium, molybdenum compound, vanadium compound, antimony compound and X element compound as a compound of an optional component element. As specific examples of methods for preparing a raw material mixture solution or slurry, there can be mentioned the following methods. An aqueous solution or slurry containing a binary mixture of ammonium metavanadate and antimony (III) oxide is heated in an atmosphere of air so as to effect a reaction. It is preferred that the aqueous solution or slurry is heated to a temperature of from 70 to 110° C. Heating of the aqueous solution or slurry may be conducted while adding water to the solution or slurry to make up for the water lost by evaporation, or conducted under reflux conditions using a reactor equipped with a condenser. It is preferred that the time for heating is 3 hours or more, especially from 4 to 50 hours. As a source of vanadium, in place of ammonium metavanadate, a solution of vanadium (V) oxide in an aqueous solution of hydrogen peroxide or an aqueous solution of the above-mentioned sources of vanadium other than ammonium metavanadate and vanadium (V) oxide also.can be used. To the aqueous solution or slurry containing the binary mixture of a vanadium compound and an antimony compound, which is obtained by the above-mentioned method, ammonium heptamolybdate or an aqueous solution thereof may be added, thereby obtaining an aqueous solution or slurry of the raw material mixture comprising a molybdenum compound, a vanadium compound and an antimony compound.

Alternatively, the raw material mixture solution or slurry can be prepared by another method described below. An aqueous solution or slurry containing a binary mixture of ammonium heptamolybdenum and antimony (III) oxide is heated so as to effect a reaction to obtain a reaction mixture, followed by addition of a vanadium compound or an aqueous solution thereof to the reaction mixture, thereby obtaining an aqueous solution or slurry of the raw material mixture comprising a molybdenum compound, a vanadium compound and an antimony compound.

When it is intended to provide an aqueous solution or slurry of a raw material mixture containing an X element compound as a compound of an optional component element, there is no particular limitation with respect to the timing to combine an X element compound with other compounds of the raw material mixture. For example, the X element compound can be added to the above-mentioned aqueous solution or slurry containing the binary mixture of a vanadium compound and an antimony compound or the binary mixture of a molybdenum compound and an antimony compound (e.g., a mixture of ammonium heptamolybdenum and antimony (III) oxide), or to the above-mentioned aqueous solution or slurry of the raw material mixture comprising a molybdenum compound, a vanadium compound and an antimony compound.

When alkoxides are used as sources of molybdenum, vanadium and/or antimony, if water is used as a liquid medium, the alkoxides are disadvantageously hydrolyzed. Therefore, when alkoxides are used as sources of molybdenum, vanadium and/or antimony, it is preferred that an alcohol is used as a liquid medium.

Step (2). Oxidation Treatment Step

In step (2) of the present invention, the raw material mixture solution or slurry prepared by the above-mentioned method is subjected to at least one oxidation treatment selected from the group consisting of (2-a) a heat treatment at 50 to 300° C. in the presence of an oxidizing gas for 1 hour or more, and (2-b) a treatment with an oxidizing liquid, thereby obtaining an oxidized raw material mixture solution or slurry.

First, an explanation is made below with respect to oxidation treatment (2-a).

There is no particular limitation with respect to the oxidizing gas. However, it is preferred to use at least one member selected from the group consisting of oxygen, air and nitrogen oxides. Nitrogen oxides mean nitrous oxide, nitrogen monoxide, nitrogen dioxide and the like. As an oxidizing gas, preferred is oxygen or air. The air may be in the form of an oxygen-rich air.

The temperature for heat treatment in oxidation treatment (2-a) is in the range of from 50 to 300° C., preferably from 50 to 200° C., more preferably from 70 to 110° C. The time for heat treatment is 1 hour or more, preferably 3 hours or more, more preferably from 4 to 15 hours.

It is preferred that heat (oxidation) treatment (2-a) of the solution or slurry of the raw material mixture in the presence of the oxidizing gas is conducted using an apparatus equipped with a reflux condenser, or an autoclave or the like under conditions wherein the drying of the raw material mixture due to the evaporation of the liquid medium will not occur.

For example, heat treatment (2-a) can be conducted by the following method. The solution or slurry of the raw material mixture is subjected to the oxidation treatment in an apparatus equipped with a reflux condenser by heating at 70 to 110° C. in the presence of the oxidizing gas. It is preferred that the solution or slurry of the raw material mixture is stirred in an atmosphere of an oxidizing gas so as to increase the area of the interface between the solution or slurry of the raw material mixture and the oxidizing gas, thereby promoting the oxidation. It is more preferred that the oxidizing gas is blown into the solution or slurry of the raw material mixture. When a reflux condenser is not used, it is preferred that an appropriate amount of water is added so that the drying of the raw material mixture does not occur. When an autoclave is used for heat treatment (2-a), heat treatment (2-a) can be conducted by a method comprising adding the solution or slurry of the raw material mixture to the autoclave, introducing the oxidizing gas into the autoclave, and subjecting the solution or slurry of the raw material mixture to the oxidation treatment at 100 to 300° C. or more. The temperature is preferably from 100 to 150° C. When an alcohol is used as a liquid medium, the heating can be conducted at 50 to 150° C. by means of an apparatus equipped with a reflux condenser. The time for heat treatment is preferably 2 hours or more, more preferably from 4 to 15 hours.

Next, explanation is made with respect to oxidation treatment (2-b).

There is no particular limitation with respect to the oxidizing liquid. However, it is preferred that the oxidizing liquid is an aqueous solution of at least one oxidizer compound selected from the group consisting of hydrogen peroxide, nitric acid and hypochlorous acid. Of these, preferred is an aqueous solution of hydrogen peroxide (i.e., aqueous hydrogen peroxide). There is no particular limitation with respect to the amount of the oxidizing liquid used. However, the molar ratio of the oxidizer compound contained in the oxidizing liquid to antimony contained in the solution or slurry of the raw material mixture is preferably 0.01 to 2, more preferably 0.1 to 1.

After the addition of the oxidizing liquid to the solution or slurry of the raw material mixture, the resultant mixture may be stirred while cooling at a temperature wherein the liquid medium is not solidified (for example, when water is used as the liquid medium, at 0 to 20° C.), at a temperature around room temperature (for example, from 20 to 30° C.) or while heating at a temperature of 100° C. or lower. When the mixture is heated to a temperature higher than the boiling point of the liquid medium, the oxidizing treatment can be conducted by means of an autoclave. The time for the oxidizing treatment is preferably 30 minutes or more, more preferably from 1 to 2 hours.

It is preferred that the solution or slurry of the oxidized raw material mixture obtained by oxidation treatment of the above-mentioned methods for (2-a) and/or (2-b) is maintained in an atmosphere of an inert gas.

With respect to the process for preparing the oxide catalyst described in the above-mentioned Unexamined Japanese Patent Application Laid-Open Specification Nos. 9-157241 and 10-28862, it is possible that, when the catalyst is produced in an atmosphere of air, in the step for the preparation of the solution or slurry of the raw material mixture comprising a Mo compound, a V compound, a Sb compound and an optionally Nb compound, the oxidation reaction may occur to some extent. However, in the above documents, any specific treatment for enhancing the oxidation state of Mo, V and Sb was not conducted. On the other hand, in the present invention, the oxidation state of Mo, V and Sb contained in the solution or slurry of the raw material mixture is extremely enhanced by subjecting the solution or slurry comprising at least Mo compound, V compound and Sb compound to the above-mentioned specific oxidation treatment. By this treatment, it becomes possible to obtain an oxide catalyst which is not only almost insusceptible to deterioration during the production of (meth)acrylonitrile, but also effective for producing (meth)acrylonitrile in high yield and high space time yield.

Step (3). X Element Compound (as a Compound of an Optional Component Element) Addition Step In step (3), an X element compound as a compound of an optional component element can be optionally added to the solution or slurry of the oxidized raw material mixture obtained in step (2). When the solution or slurry of the raw material mixture containing an unsatisfactory amount of an X element compound is prepared in step (1), an appropriate amount of the X element compound is supplementarily added, in step (3), to the solution or slurry of the oxidized raw material mixture obtained in step (2) prior to the below-mentioned drying process. When the solution or slurry of the raw material mixture provided in the above-mentioned step (1) contains an X element compound, the X element compound may or may not be oxidized during the above-mentioned oxidation treatment step, depending on the type of the X element compound. However, whether or not the X element compound is oxidized has no influence on the effects of the present invention.

Step (4). Drying Step

In step (4) of the process of the present invention, the above-mentioned solution or slurry of the oxidized raw material mixture is dried so as to obtain a dried catalyst precursor.

The drying of the solution or slurry of the oxidized raw material mixture can be conducted by a known method, such as spray drying or evaporation drying. The spray drying can be conducted, for example, by spraying and heating the solution or slurry of the oxidized raw material mixture in the dryer. The spray drying can be conducted by centrifugation, by the two-phase flow nozzle method or by the high pressure nozzle method. As a heat source for drying, it is preferred to use air which has been heated by steam, an electric heater and the like. It is preferred that the temperature of the dryer at an entrance to the dryer section thereof is from 150 to 300° C. The spray drying can be also conveniently conducted by spraying the solution or slurry of the oxidized raw material mixture onto an iron plate which has been heated to a temperature of 100 to 300° C.

The solution or slurry of the oxidized raw material mixture can be evaporation-dried by heating it in a vessel, such as a beaker, at 100 to 300° C. The time for heating varies depending on the composition or amount of the solution or slurry of the oxidized raw material, but is generally from 5 minutes to 20 hours, preferably from 5 minutes to 3 hours.

The dried catalyst precursor can be obtained in a powder form by the above-mentioned drying step.

Step (5). Calcination Step

In step (5) of the process of the present invention, the above-mentioned dried catalyst precursor is calcined so as to obtain an oxide catalyst comprising component oxide represented by formula (1) above.

The calcination can be conducted by a known method. For example, use can be made of a kiln, such as a rotary kiln, a tunnel kiln, a muffle kiln or a fluidized firing kiln. The calcination is generally conducted in an atmosphere of an inert gas, such as nitrogen gas under atmospheric pressure, which is substantially free of oxygen, preferably under a flow of an inert gas, at a temperature of 400 to 700° C., preferably 500 to 700° C., more preferably 550 to 650° C. The time of calcination is generally 0.5 to 5 hours, preferably 1 to 3 hours. It is preferred that the oxygen concentration in the above-mentioned inert gas is 1000 ppm or less, more preferably 100 ppm or less as measured by gas chromatography or by means of a trace oxygen analyzer. The calcination can be conducted repeatedly. Prior to the calcination, the dried catalyst precursor may be subjected to pre-calcination in an atmosphere of air or under a stream of air at 200 to 420° C., preferably 250 to 350° C. for 10 minutes to 5 hours. The catalyst obtained by calcination may be subjected to further calcination in an atmosphere of air at a temperature of from 200 to 400° C. for 5 minutes to 5 hours. The catalyst obtained by calcination may be pulverized and subjected to further calcination.

When it is intended to produce a silica-supported catalyst, the addition of a silica sol can be made at an any time in the above-mentioned steps (1) and (2). The amount of silica is generally in the range of from 20 to 60% by weight, preferably 20 to 40% by weight, based on the total weight of the catalyst and silica. It is preferred to use a silica sol stabilized by ammonium ions to prevent gelation. It is preferred that the silica sol contains ammonium ions in an amount sufficient for keeping the pH of the silica sol at around 9.7.

The oxide catalyst obtained by the process of the present invention which comprises the above-mentioned steps (1) to (5), as such, can be advantageously used for producing (meth)acrylonitrile in high yield and in high space time yield. However, when use is made of a base-treated oxide catalyst obtained by the process according to another aspect of the present invention which further comprises the steps of (6) contacting the above-mentioned oxide catalyst with an aqueous basic solution to obtain a contact mixture containing a base-treated oxide catalyst, and (7) separating and recovering said base-treated oxide catalyst from the contact mixture, it has become possible to produce (meth) acrylonitrile in further improved yield and space time yield. In this connection, it should be noted that, by this embodiment, it has also become possible to suppress the decomposition of ammonia, which is one of the materials for the production of (meth)acrylonitrile, into nitrogen. The reason why such excellent effects can be obtained has not yet been elucidated. However, it is considered to be as follows: The oxide catalyst obtained in step (5) contains undesired, noneffective phases of component oxides, such as a noncrystalline molybdenum oxide, and these undesired, noneffective phases of component oxides induce the burning or decomposition of ammonia or (meth)acrylonitrile. However, by the treatment with an aqueous basic solution, the above-mentioned undesired, noneffective phases of component oxides can be removed, so that not only are the yield and space time yield of (meth)acrylonitrile improved, but also the decomposition of ammonia into nitrogen is suppressed.

Hereinbelow, explanation is made with respect to the above-mentioned steps (6) and (7) for the treatment with an aqueous basic solution.

In step (6), the oxide catalyst is contacted with the aqueous basic solution so as to obtain a contact mixture comprising a base-treated oxide catalyst.

Examples of basic substances contained in the aqueous basic solution include ammonia; hydroxides, carbonates and organic acid salts (for example, oxalates, acetates and citrates) of alkali metals, such as lithium, sodium, potassium, rubidium, cesium and the like; hydroxides, carbonates and organic acid salts (for example, oxalates, acetates and citrates) of alkaline earth metals, such as beryllium, magnesium, calcium, strontium, barium and the like; and amines, such as ethylamine, methylamine and the like. Especially preferred is aqueous ammonia. The concentration of the basic substance in the aqueous basic solution is generally in the range of from 0.1 to 30% by weight, preferably from 1 to 10% by weight.

As examples of the methods for contacting the oxide catalyst with the aqueous basic solution, there can be mentioned a batchwise operation method and a flow operation method.

When the batchwise operation method is employed, the oxide catalyst is suspended in the aqueous basic solution in a tank reactor so as to obtain a contact mixture in the form of a suspension.

The weight ratio of the catalyst to the aqueous basic solution is preferably in the range of from 1 to 20% by weight. There is no particular limitation with respect to the period during which the oxide catalyst is in contact with the aqueous basic solution. However, preferred is 2 hours or more, more preferred is 6 hours or more. It is preferred that the temperature of the aqueous basic solution is in the range of from 0 to 100° C. When aqueous ammonia is used as the aqueous basic solution, it is more preferred that the temperature of the aqueous basic solution is in the range of from 0 to 50° C. For effectively performing an intimate contact of the oxide catalyst with the aqueous basic solution, it is preferred to stir the contact mixture by means of a stirrer or blow a gas into the contact mixture. There is no particular limitation with respect to the above-mentioned gas. However, it is preferred to use a gas which would not change the aqueous basic solution to a neutral solution. Examples of such gases include air, nitrogen gas and a rare gas. As an example of the flow operation method, there can be mentioned a method in which the aqueous basic solution is flowed through a fixed bed formed by charging the oxide catalyst in a reactor.

In step (7), the base-treated oxide catalyst is separated and recovered from the contact mixture. The separation can be conducted by centrifugation, filtration using a filter paper or a filter membrane, decantation and the like. It is preferred that the oxide catalyst separated and recovered from the above-mentioned contact mixture is washed with water, followed by drying. The drying after the above-mentioned treatment with the aqueous basic solution can be conducted, using a heated air dryer, a constant temperature chamber or the like, at 100 to 150° C.

Further, in the process of the present invention, as step (8), it is preferred to calcine the base-treated oxide catalyst recovered in the above-mentioned step (7). The calcination after the treatment with the aqueous basic solution can be performed under the same conditions as in the calcination of the above-mentioned step (5). That is, the calcination can be, conducted in an atmosphere of an inert gas, such as nitrogen gas or the like, which is substantially free of oxygen, preferably under a flow of an inert gas, at 400 to 700° C., preferably 500 to 700° C., more preferably 550 to 650° C.

The operation comprising the treatment using the aqueous basic solution in the above-mentioned steps (6) and (7) and subsequent calcination in the above-mentioned step (8) can be repeatedly conducted so as to further improve the yield and space time yield of (meth)acrylonitrile.

Hereinbelow, explanation is made with respect to the process, for producing (meth)acrylonitrile from propane or isobutane by ammoxidation in the gaseous phase in the presence of the oxide catalyst comprising the compound oxide prepared by the process of the present invention.

The feedstock mixture comprising propane or isobutane and ammonia need not be of a very high purity but may be of a commercial grade.

Examples of sources of oxygen include air, oxygen-rich air, and pure oxygen. Further, such a source of molecular oxygen may be diluted with helium, argon, nitrogen, carbon dioxide, steam or the like.

The molar ratio of ammonia to propane or isobutane for the ammoxidation may be generally in the range of from 0.1 to 1.5, preferably from 0.2 to 1.2.

The molar ratio of molecular oxygen to propane or isobutane used for the ammoxidation may be generally in the range of from 0.2 to 6, preferably from 0.4 to 4.

The ammoxidation pressure is generally in the range of from 0.1 to 10 atm, preferably from 1 to 3 atm.

The ammoxidation temperature is generally in the range of from 350 to 600° C., preferably from 380 to 470° C.

The time of contact (contact time) between the gaseous feedstocks and the catalyst is generally in the range of from 0.1 to 30 (g·sec/ml), preferably from 0.5 to 10 (g·sec/ml).

In the process of the present invention, the contact time is determined according to the following formula:

Contact time(g·sec/ml)

$$\text{Contact time (g·sec/ml)} = (W/F) \times 60 \times \frac{273}{(273+T)} \times P$$

wherein:
  W represents the weight (g) of the catalyst contained in the reactor;
  F represents the flow rate (ml/s) of the raw material mixture gas {as measured under normal temperature and pressure conditions (0° C., 1 atm)};
  T represents the ammoxidation reaction temperature (° C.); and P represents the ammoxidation reaction pressure (atm).

The reaction of the present invention can be conducted in a conventional reactor, such as a fixed bed reactor, a fluidized-bed reactor or a moving bed reactor.

The reaction mode employed in the process of the present invention may be either a one pass mode or a recycling mode.

BEST MODE FOR CARRYING OUT THE INVENTION

Hereinbelow, the present invention will be described in more detail with reference to the following Examples and Comparative Examples, which are for illustrative purposes only, and should not be construed as limiting the scope of the present invention.

In the following Examples and Comparative Examples, the conversion (%) of propane, the selectivity (%) for acrylonitrile, the yield (%) of acrylonitrile, the space time yield [$\mu$mol/{(g·sec/ml)·g}] of acrylonitrile and the ammonia decomposition ratio (%), each used for evaluating the results of the ammoxidation of propane, are defined as follows:

$$\text{Conversion (\%) of propane} = \frac{\text{(mole of propane reacted)}}{\text{(mole of propane fed)}} \times 100$$

$$\text{Selectivity (\%) for acrylonitrile} = \frac{\text{(mole of acrylonitrile formed)}}{\text{(mole of propane reacted)}} \times 100$$

$$\text{Yield (\%) of acrylonitrile} = \frac{\text{(mole of acrylonitrile formed)}}{\text{(mole of propane fed)}} \times 100$$

Space time yield [$\mu$mol/{(g·sec/ml)·g}] of acrylonitrile =

$$\frac{\text{mole of acrylonitrile formed (}\mu\text{mol)}}{\text{contact time (g·sec/ml)} \times \text{catalyst weight (g)}} \times 100$$

$$\text{Ammonia decomposition ratio (\%)} = \frac{2 \times \text{(mole of nitrogen formed)}}{\text{(mole of ammonia fed)}} \times 100$$

EXAMPLE 1

Preparation of an Oxide Catalyst

An oxide catalyst comprising a compound oxide represented by the formula:

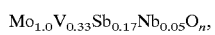

$Mo_{1.0}V_{0.33}Sb_{0.17}Nb_{0.05}O_n$, wherein n is a number determined by and consistent with the valence requirements of the other elements present in the compound oxide of the above formula, which applies to n appearing in the formulae representing the compound oxides obtained in all of the subsequent Examples and Comparative Examples, was prepared as follows.

2.19 g of ammonium metavanadate ($NH_4VO_3$) and 1.41 g of antimony(III) oxide ($Sb_2O_3$) were added to 80 g of water, and the resultant mixture was heated at 100° C. for 24 hours under reflux, using an oil bath, under atmospheric pressure while stirring. Then, to the resultant binary mixture slurry was added 10.0 g of ammonium heptamolybdate [($NH_4$)$_6Mo_7O_{24}$·$4H_2O$], to thereby obtain a raw material mixture solution containing molybdenum (Mo), vanadium (V) and antimony (Sb). The obtained raw material mixture solution was subjected to an oxidation treatment wherein the solution was stirred for 4 hours, using a water bath, in an atmosphere of air under atmospheric pressure while maintaining the temperature of the solution at 85° C., to thereby obtain an oxidized raw material mixture solution. The obtained oxidized raw material mixture solution was cooled to room temperature.

Separately, 0.50 g of a niobic acid ($Nb_2O_5$ content: 76% by weight) and 0.96 g of oxalic acid dihydrate ($H_2C_2O_4$·$2H_2O$) were dissolved in 25 g of water at 70° C., and the resultant solution was cooled to 30° C. over 30 min, to thereby obtain a niobium-containing aqueous solution. The obtained niobium-containing aqueous solution was added to the oxidized raw material mixture solution obtained above and stirred in an atmosphere of air at 30° C. for 30 min, to thereby obtain a niobium-containing oxidized raw material mixture solution.

The obtained niobium-containing oxidized raw material mixture solution was subjected to spray drying wherein the solution was sprayed onto a Teflon-coated iron plate heated to 140° C., to thereby obtain a dried particulate catalyst precursor. 2.2 g of the obtained catalyst precursor was subjected to heat treatment under a stream of air for 1 hour using a thermostat set at 300° C. The resultant catalyst precursor was charged into a quartz tube having an inner diameter of 20 mm, and then calcined at 600° C. for 2 hours under a stream of nitrogen gas at a flow rate of 350 Nml/min (Nml means ml as measured under the normal temperature and pressure conditions, namely at 0° C. under 1 atm), to thereby obtain an oxide catalyst comprising a compound oxide of the above formula.

With respect to the oxygen concentration of the nitrogen gas used for the calcination, measurement was done by means of a trace oxygen analyzer (type 306WA; manufactured and sold by Teledyne Analytical Instruments, U.S.A). As a result, it was found that the oxygen concentration of the nitrogen gas was 1 ppm.

Ammoxidation of Propane

An ammoxidation of propane was performed in the presence of the above-obtained oxide catalyst in a manner as described below.

0.3 g of the obtained catalyst was charged into a fixed-bed reaction tube having an inner diameter of 4 mm. In the reaction tube containing the catalyst, an ammoxidation of propane was performed under conditions wherein the temperature (T) was 430° C., the flow rate (F) of a gaseous feedstock mixture (i.e., a gaseous mixture of propane, ammonia, molecular oxygen and helium) was 5.5 Nml/min, the [propane:ammonia:molecular oxygen:helium] molar ratio in the gaseous feedstock mixture was 1:1.2:2.8:12, the pressure (P) was 1 atm, and the time of contact (contact time) between the catalyst and the gaseous feedstock mixture was 1.17 g·sec/ml. The produced gaseous reaction mixture was subjected to analysis by means of an on-line gas chromatography apparatus (GC-14B; manufactured and sold by Shimadzu Corporation, Japan). The results of the above ammoxidation are shown in Table 1.

EXAMPLE 2

Preparation of an Oxide Catalyst

An oxide catalyst comprising a compound oxide represented by the formula:

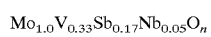

$Mo_{1.0}V_{0.33}Sb_{0.17}Nb_{0.05}O_n$ was prepared in substantially the same manner as in Example 1, except that the raw material mixture solution was subjected to an oxidation treatment wherein the solution was stirred for 6 hours, using a water bath, in an atmosphere of air under atmospheric pressure while maintaining the temperature of the solution at 100° C., followed by cooling to room temperature.

Ammoxidation of Propane

An ammoxidation of propane was performed in the presence of the oxide catalyst obtained above under the same conditions as in Example 1. The results of the ammoxidation are shown in Table 1.

EXAMPLE 3

Preparation of an Oxide Catalyst

An oxide catalyst comprising a compound oxide represented by the formula:

$Mo_{1.0}V_{0.33}Sb_{0.17}Nb_{0.05}O_n$ was prepared in substantially the same manner as in Example 1, except that the raw material mixture solution was subjected to an oxidation treatment wherein the solution was stirred for 8 hours, using a water bath, in an atmosphere of air under atmospheric pressure while maintaining the temperature of the solution at 75° C.

Ammoxidation of Propane

An ammoxidation of propane was performed in the presence of the oxide catalyst obtained above under the same conditions as in Example 1, except that the flow rate (F) of the gaseous feedstock mixture was changed to 4.3 Nml/min and the contact time was changed to 1.50 g·sec/ml. The results of the ammoxidation are shown in Table 1.

EXAMPLE 4

Preparation of an Oxide Catalyst

An oxide catalyst comprising a compound oxide represented by the formula:

$Mo_{1.0}V_{0.33}Sb_{0.17}Nb_{0.05}O_n$ was prepared in substantially the same manner as in Example 1, except that the raw material mixture solution was subjected to an oxidation treatment wherein the solution was stirred for 10 hours, using a water bath, in an atmosphere of air under atmospheric pressure while maintaining the temperature of the solution at 95° C.

Ammoxidation of Propane

An ammoxidation of propane was performed in the presence of the oxide catalyst obtained above under the same conditions as in Example 1. The results of the ammoxidation are shown in Table 1.

EXAMPLE 5

Preparation of an Oxide Catalyst

An oxide catalyst comprising a compound oxide represented by the formula:

$Mo_{1.0}V_{0.33}Sb_{0.17}Nb_{0.05}O_n$ was prepared in substantially the same manner as in Example 1, except that the raw material mixture solution was subjected to an oxidation treatment wherein the solution was charged into a 500 ml autoclave having a Teflon lining on the inner wall thereof and sealed up together with air in the autoclave, followed by stirring at 150° C. under a pressure of 0.8 MPa for 2 hours.

Ammoxidation of Propane

An ammoxidation of propane was performed in the presence of the oxide catalyst obtained above under the same conditions.as in Example 1, except that the flow rate (F) of the gaseous feedstock mixture was changed to 4.6 Nml/min and the contact time was changed to 1.40 g·sec/ml. The results of the ammoxidation are shown in Table 1.

EXAMPLE 6

Preparation of an Oxide Catalyst

An oxide catalyst comprising a compound oxide represented by the formula:

$Mo_{1.0}V_{0.33}Sb_{0.17}Nb_{0.05}O_n$ was prepared in substantially the same manner as in Example 1, except that the raw material mixture solution was subjected to an oxidation treatment wherein 0.8 g of 5% (w/w) aqueous hydrogen peroxide was added to the raw material mixture solution and stirred at 30° C. under atmospheric pressure for 30 min.

In the above oxidation treatment, the molar ratio of hydrogen peroxide ($H_2O_2$) contained in the aqueous hydrogen peroxide used to antimony (Sb) contained in the raw material mixture solution (hereinafter, frequently referred to simply as "[$H_2O_2$:Sb] molar ratio") was 0.12.

Ammoxidation of Propane

An ammoxidation of propane was performed in the presence of the oxide catalyst obtained above under the same conditions as in Example 1. The results of the ammoxidation are shown in Table 1.

EXAMPLE 7

Preparation of an Oxide Catalyst

An oxide catalyst comprising a compound oxide represented by the formula:

$Mo_{1.0}V_{0.33}Sb_{0.17}Nb_{0.05}O_n$ was prepared in substantially the same manner as in Example 6, except that the raw material mixture solution was subjected to an oxidation treatment wherein 3.4 g of 5% (w/w) aqueous hydrogen peroxide was added to the raw material mixture solution and stirred at 30° C. under atmospheric pressure for 1 hour. In the above oxidation treatment, the [$H_2O_2$:Sb] molar ratio was 0.52.

Ammoxidation of Propane

An ammoxidation of propane was performed in the presence of the oxide catalyst obtained above under the same conditions as in Example 1. The results of the ammoxidation are shown in Table 2.

EXAMPLE 8

Preparation of an Oxide Catalyst

An oxide catalyst comprising a compound oxide represented by the formula:

$Mo_{1.0}V_{0.33}Sb_{0.17}Nb_{0.05}O_n$ was prepared in substantially the same manner as in Example 6, except that the raw material mixture solution was subjected to an oxidation treatment wherein 2.0 g of 5% (w/w) aqueous hydrogen peroxide was added to the raw material mixture solution and stirred at 20° C. under atmospheric pressure for 2 hours. In the above oxidation treatment, the [$H_2O_2$:Sb] molar ratio was 0.30.

Ammoxidation of Propane

An ammoxidation of propane was performed in the presence of the oxide catalyst obtained above under the same conditions as in Example 1. The results of the ammoxidation are shown in Table 2.

EXAMPLE 9

Preparation of an Oxide Catalyst

An oxide catalyst comprising a compound oxide represented by the formula:

$$Mo_{1.0}V_{0.33}Sb_{0.17}Nb_{0.05}O_n$$

was prepared in substantially the same manner as in Example 6, except that the raw material mixture solution was subjected to an oxidation treatment wherein 5.5 g of 5% (w/w) aqueous hydrogen peroxide was added to the raw material mixture solution and stirred in an atmosphere of air at 25° C. under atmospheric pressure for 45 min. In the above oxidation treatment, the [$H_2O_2$:Sb] molar ratio was 0.83.

Ammoxidation of Propane

An ammoxidation of propane was performed in the presence of the oxide catalyst obtained above under the same conditions as in Example 1. The results of the ammoxidation are shown in Table 2.

EXAMPLE 10

Preparation of an Oxide Catalyst

An oxide catalyst comprising a silica carrier having supported thereon a compound oxide (silica carrier content: 30% by weight in terms of $SiO_2$, based on the total weight of the compound oxide and the silica carrier), in which the compound oxide is represented by the formula:

$$Mo_{1.0}V_{0.26}Sb_{0.13}Nb_{0.05}O_n$$

was prepared as follows.

0.86 g of ammonium metavanadate ($NH_4VO_3$) and 0.54 g of antimony(III) oxide ($Sb_2O_3$) were added to 50 g of water, and the resultant mixture was heated at 120° C. for 8 hours under reflux, using an oil bath, in an atmosphere of air under atmospheric pressure while stirring. Then, to the resultant binary mixture slurry was added 5.00 g of ammonium heptamolybdate [$(NH_4)_6Mo_7O_{24} \cdot 4H_2O$], to thereby obtain a raw material mixture solution containing Mo, V and Sb. The obtained raw material mixture solution was subjected to an oxidation treatment wherein the solution was stirred for 4 hours, using a water bath, in an atmosphere of air under atmospheric pressure while maintaining the temperature of the solution at 80° C., to thereby obtain an oxidized raw material mixture solution. After completion of the stirring, no white precipitate was observed in the oxidized raw material mixture solution.

The obtained oxidized raw material mixture solution was cooled to 30° C., and then, to the resultant solution was added 0.96 g of 30% (w/w) aqueous hydrogen peroxide and stirred for 40 min, to thereby effect a further oxidation treatment. In this further oxidation treatment, the [$H_2O_2$:Sb] molar ratio was 2.3. To the resultant oxidized raw material mixture solution was added 7.89 g of a silica sol having an $SiO_2$ content of 30% by weight while stirring, to thereby obtain a silica-containing oxidized raw material mixture solution.

Separately, 0.25 g of a niobic acid ($Nb_2O_5$ content: 76% by weight) and 0.48 g of oxalic acid dihydrate ($H_2C_2O_4 \cdot 2H_2O$) were dissolved in 5.0 g of water at 70° C., and the resultant solution was cooled to 30° C., to thereby obtain a niobium-containing aqueous solution. The obtained niobium-containing aqueous solution was added to the silica-containing oxidized raw material mixture solution obtained above and stirred in an atmosphere of air at 30° C. for 30 min, to thereby obtain an oxidized raw material mixture solution containing niobium and silica.

The obtained oxidized raw material mixture solution containing niobium and silica was subjected to spray drying wherein the solution was sprayed onto a Teflon-coated iron plate heated to 140° C., to thereby obtain a dried particulate catalyst precursor. 2.2 g of the obtained catalyst precursor was subjected to heat treatment under a stream of air for 1 hour using a thermostat set at 300° C. The resultant catalyst precursor was charged into a quartz tube having an inner diameter of 20 mm, and then calcined at 600° C. for 2 hours under a stream of nitrogen gas at a flow rate of 350 Nml/min, to thereby obtain an oxide catalyst comprising a silica carrier having supported thereon a compound oxide of the above formula.

With respect to the oxygen concentration of the nitrogen gas used for the calcination, measurement was done by means of a trace oxygen analyzer (type 306WA; manufactured and sold by Teledyne Analytical Instruments, U.S.A). As a result, it was found that the oxygen concentration of the nitrogen gas was 1 ppm.

Ammoxidation of Propane

An ammoxidation of propane was performed in the presence of the above-obtained oxide catalyst comprising the silica carrier having supported thereon the compound oxide in a manner as described below.

0.3 g of the obtained catalyst was charged into a fixed-bed reaction tube having an inner diameter of 4 mm. In the reaction tube containing the catalyst, an ammoxidation of propane was performed under conditions wherein the temperature (T) was 430° C., the flow rate (F) of a gaseous feedstock mixture (i.e., a gaseous mixture of propane, ammonia, molecular oxygen and helium) was 5.0 Nml/min, the [propane:ammonia:molecular oxygen:helium] molar ratio in the gaseous feedstock mixture was 1:0.95:2.57:10.65, the pressure (P) was 1 atm, and the time of contact (contact time) between the catalyst and the gaseous feedstock mixture was 1.29 g·sec/ml. The produced gaseous reaction mixture was subjected to analysis by means of an on-line gas chromatography apparatus (GC-14B; manufactured and sold by Shimadzu Corporation, Japan). The results of the above ammoxidation are shown in Table 2.

EXAMPLE 11

Preparation of an Oxide Catalyst

An oxide catalyst comprising a compound oxide represented by the formula:

$$Mo_{1.0}V_{0.3}Sb_{0.13}Ti_{0.06}O_n$$

was prepared as follows.

5.48 g of ammonium metavanadate ($NH_4VO_3$) and 2.96 g of antimony(III) oxide ($Sb_2O_3$) were added to 109.5 g of water, and the resultant mixture was heated at 100° C. for 8 hours under reflux, using an oil bath, in an atmosphere of air under atmospheric pressure while stirring. Then, to the resultant binary mixture slurry was added 27.47 g of ammonium heptamolybdate $[(NH_4)_6Mo_7O_{24}\cdot 4H_2O]$, to thereby obtain a raw material mixture solution containing Mo, V and Sb. The obtained raw material mixture solution was subjected to an oxidation treatment wherein the solution was stirred for 4 hours, using a water bath, in an atmosphere of air under atmospheric pressure while maintaining the temperature of the solution at 80° C., to thereby obtain an oxidized raw material mixture solution. After completion of the stirring, no white precipitate was observed in the oxidized raw material mixture solution.

The obtained oxidized raw material mixture solution was cooled to 30° C., and then, to the resultant solution was added 0.96 g of 30% (w/w) aqueous hydrogen peroxide and stirred for 40 min, to thereby effect a further oxidation treatment. In this further oxidation treatment, the $[H_2O_2:Sb]$ molar ratio was 0.42.

Separately, 2.44 g of ammonium titanyl oxalate $[(NH_4)_2TiO(C_2O_4)_2]$ was dissolved in 12.5 g of water, and the resultant solution was added to the oxidized raw material mixture solution obtained by the above further oxidation treatment and stirred in an atmosphere of air at 30° C. for 30 min, to thereby obtain a titanium-containing oxidized raw material mixture solution.

The obtained titanium-containing oxidized raw material mixture solution was subjected to spray drying wherein the solution was sprayed onto a Teflon-coated iron plate heated to 140° C., to thereby obtain a dried particulate catalyst precursor. 3.0 g of the obtained catalyst precursor was subjected to heat treatment under a stream of air for 1 hour using a thermostat set at 300° C. The resultant catalyst precursor was charged into a quartz tube having an inner diameter of 20 mm, and then calcined at 600° C. for 2 hours under a stream of nitrogen gas at a flow rate of 350 Nml/min, to thereby obtain an oxide catalyst comprising a compound oxide of the above formula.

With respect to the oxygen concentration of the nitrogen gas used for the calcination, measurement was done by means of a trace oxygen analyzer (type 306WA; manufactured and sold by Teledyne Analytical Instruments, U.S.A). As a result, it was found that the oxygen concentration of the nitrogen gas was 1 ppm.

Ammoxidation of Propane

An ammoxidation of propane was performed in the presence of the above-obtained oxide catalyst in a manner as described below.

1.5 g of the obtained catalyst was charged into a fixed-bed reaction tube having an inner diameter of 9.5 mm. In the reaction tube containing the catalyst, an ammoxidation of propane was performed under conditions wherein the temperature (T) was 430° C., the flow rate (F) of a gaseous feedstock mixture (i.e., a gaseous mixture of propane, ammonia, molecular oxygen and helium) was 23.3 Nml/min, the [propane:ammonia:molecular oxygen:helium] molar ratio in the gaseous feedstock mixture was 1:1.2:2.7:12.3, the pressure (P) was 1 atm, and the time of contact (contact time) between the catalyst and the gaseous feedstock mixture was 1.67 g·sec/ml. The produced gaseous reaction mixture was subjected to analysis by means of an on-line gas chromatography apparatus (GC-14B; manufactured and sold by Shimadzu Corporation, Japan). The results of the above ammoxidation are shown in Table 2.

COMPARATIVE EXAMPLE 1

Preparation of an Oxide Catalyst

An oxide catalyst comprising a compound oxide represented by the formula:

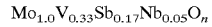
$Mo_{1.0}V_{0.33}Sb_{0.17}Nb_{0.05}O_n$ was prepared in substantially the same manner as in Example 1, except that the oxidation treatment of the raw material mixture solution was omitted and, instead, the solution was cooled to 30° C. over 30 min using a water bath.

Ammoxidation of Propane

An ammoxidation of propane was performed in the presence of the oxide catalyst obtained above under the same conditions as in Example 1, except that the flow rate (F) of the gaseous feedstock mixture was changed to 2.75 Nml/min and the contact time was changed to 2.33 g·sec/ml. The results of the ammoxidation are shown in Table 2.

COMPARATIVE EXAMPLE 2

Preparation of an Oxide Catalyst

An oxide catalyst comprising a silica carrier having supported thereon a compound oxide (silica carrier content: 30% by weight in terms of $SiO_2$, based on the total weight of the compound oxide and the silica carrier), in which the compound oxide is represented by the formula:

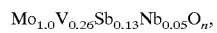
$Mo_{1.0}V_{0.26}Sb_{0.13}Nb_{0.05}O_n$, was prepared in substantially the same manner as in Example 10, except that the oxidation treatment of the raw material mixture solution (wherein the solution was heated in an atmosphere of air) was omitted and, instead, the raw material mixture solution was immediately cooled to 30° C., and that the addition of the aqueous hydrogen peroxide was omitted.

Ammoxidation of Propane

An ammoxidation of propane was performed in the presence of the above-obtained oxide catalyst comprising the silica carrier having supported thereon the compound oxide under the same conditions as in Example 10. The results of the ammoxidation are shown in Table 2.

COMPARATIVE EXAMPLE 3

Preparation of an Oxide Catalyst

An oxide catalyst comprising a compound oxide represented by the formula:

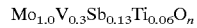
$Mo_{1.0}V_{0.3}Sb_{0.13}Ti_{0.06}O_n$ was prepared in substantially the same manner as in Example 11, except that the oxidation treatment of the raw material mixture solution (wherein the solution was heated in an atmosphere of air) was omitted and, instead, the raw material mixture solution was immediately cooled to 10° C., and that the addition of the aqueous hydrogen peroxide was omitted.

Ammoxidation of Propane

An ammoxidation of propane was performed in the presence of the oxide catalyst obtained above under the same conditions as in Example 11. The results of the ammoxidation are shown in Table 2.

EXAMPLE 12

Preparation of an Oxide Catalyst

An oxide catalyst comprising a compound oxide represented by the formula:

$$Mo_{1.0}V_{0.29}Sb_{0.14}Nb_{0.06}O_n$$

was prepared as follows.

1.92 g, of ammonium metavanadate ($NH_4VO_3$) and 1.16 g of antimony(III) oxide ($Sb_2O_3$) were added to 80 g of water, and the resultant mixture was heated at 100° C. for 8 hours under reflux; using an oil bath, in an atmosphere of air under atmospheric pressure while stirring. Then, to the resultant binary mixture slurry was added 10.0 g of ammonium heptamolybdate [$(NH_4)_6Mo_7O_{24}.4H_2O$], to thereby obtain a raw material mixture solution containing Mo, V and Sb. The obtained raw material mixture solution was subjected to an oxidation treatment wherein the solution was stirred for 4 hours, using a water bath, in an atmosphere of air under atmospheric pressure while maintaining the temperature of the solution at 85° C., to thereby obtain an oxidized raw material mixture solution. The obtained oxidized raw material mixture solution was cooled to room temperature.

Separately, 0.60 g of a niobic acid ($Nb_2O_5$ content: 76% by weight) and 0.96 g of oxalic acid dihydrate ($H_2C_2O_4.2H_2O$) were dissolved in 25 g of water at 70° C., and the resultant solution was cooled to 30° C., to thereby obtain a niobium-containing aqueous solution. The obtained niobium-containing aqueous solution was added to the oxidized raw material mixture solution obtained above and stirred in an atmosphere of air at 30° C. for 30 min, to thereby obtain a niobium-containing oxidized raw material mixture solution.

The obtained niobium-containing oxidized raw material mixture solution was subjected to spray drying wherein the solution was sprayed onto a Teflon-coated iron plate heated to 140° C., to thereby obtain a dried particulate catalyst precursor. 12.0 g of the obtained catalyst precursor was subjected to heat treatment under a stream of air for 1 hour using a thermostat set at 300° C. The resultant catalyst precursor was charged into a quartz tube having an inner diameter of 20 mm, and then calcined at 600° C. for 2 hours under a stream of nitrogen gas at a flow rate of 350 Nml/min, to thereby obtain an oxide catalyst comprising a compound oxide of the above formula.

With respect to the oxygen concentration of the nitrogen gas used for the calcination, measurement was done by means of a trace oxygen analyzer (type 306WA; manufactured and sold by Teledyne Analytical Instruments, U.S.A). As a result, it was found that the oxygen concentration of the nitrogen gas was 1 ppm.

Ammoxidation of Propane

An ammoxidation of propane was performed in the presence of the above-obtained oxide catalyst in a manner as described below.

0.3 g of the obtained catalyst was charged into a fixed-bed reaction tube having an inner diameter of 4 mm. In the reaction tube containing the catalyst, an ammoxidation of propane was performed under conditions wherein the temperature (T) was 430° C., the flow rate (F) of a gaseous feedstock mixture (i.e., a gaseous mixture of propane, ammonia, molecular oxygen and helium) was 6 Nml/min, the [propane:ammonia:molecular oxygen:helium] molar ratio in the gaseous feedstock mixture was 1:1.2:2.9:11.9, the pressure (P) was 1 atm, and the time of contact (contact time) between the catalyst and the gaseous feedstock mixture was 1.17 g·sec/ml. The produced gaseous reaction mixture was subjected to analysis by means of an on-line gas chromatography apparatus. The results of the above ammoxidation are shown in Table 3.

EXAMPLE 13

Treatment of an Oxide Catalyst with an Aqueous Basic Solution 3.0 g of the oxide catalyst obtained in Example 12 was added to 50.0 g of 5% by weight aqueous ammonia, and then, the resultant suspension was stirred in an atmosphere of air at 25° C. under atmospheric pressure for 8 hours to thereby obtain a suspension containing a base-treated oxide catalyst. The obtained suspension was subjected to filtration under suction to separate and remove the aqueous ammonia from the base-treated oxide catalyst, so that the base-treated oxide catalyst was recovered from the suspension. After the filtration, the recovered catalyst was washed four times with 50 ml of pure water, and dried in a thermostat set at 200° C. under a stream of air. All of the dried catalyst was charged into a quartz tube having an inner diameter of 20 mm, and then calcined at 550° C. for 2 hours under a stream of nitrogen gas at a flow rate of 350 Nml/mini to thereby obtain a base-treated, calcined oxide catalyst. The nitrogen gas used in the calcination was the same as used in the calcination in Example 12.

Ammoxidation of Propane

An ammoxidation of propane was performed in the presence of the base-treated, calcined oxide catalyst obtained above under the same conditions as in Example 12. The results of the ammoxidation are shown in Table 3.

EXAMPLE 14

Treatment of an Oxide Catalyst with an Aqueous Basic Solution 4.5 g of the oxide catalyst obtained in Example 12 was added to 80.0 g of 5% by weight.aqueous ammonia, and then, the resultant suspension was stirred in an atmosphere of air at 25° C. under atmospheric pressure for 15 hours, to thereby obtain a suspension containing a base-treated oxide catalyst. The obtained suspension was subjected to filtration under suction to separate and remove the aqueous ammonia from the base-treated oxide catalyst, so that the base-treated oxide catalyst was recovered from the suspension. After the filtration, the recovered catalyst was washed four times with 50 ml of pure water, and dried in a thermostat set at 200° C. under a stream of air. All of the dried catalyst was charged into a quartz tube having an inner diameter of 20 mm, and then calcined at 550° C. for 2 hours under a stream of nitrogen gas at a flow rate of 500 Nml/min, to thereby obtain a base-treated, calcined oxide catalyst. The nitrogen gas used in the calcination was the same as used in the calcination in Example 12.

Ammoxidation of Propane

An ammoxidation of propane was performed in the presence of the base-treated, calcined oxide catalyst obtained above under the same conditions as in Example 12, except that the flow rate (F) of the gaseous feedstock mixture was changed to 6.4 Nml/min and the contact time was changed to 1.10 g·sec/ml. The results of the ammoxidation are shown in Table 3.

EXAMPLE 15

Preparation of an Oxide Catalyst

An oxide catalyst comprising a compound oxide represented by the formula:

$$Mo_{1.0}V_{0.31}Sb_{0.14}Nb_{0.05}O_n$$

was prepared in substantially the same manner as in Example 12, except that 2.05 g of ammonium metavanadate ($NH_4VO_3$) was used, 1.16 g of antimony(III) oxide ($Sb_2O_3$) was used and 0.50 g of a niobic acid ($Nb_2O_5$ content: 76% by weight) was used.

Ammoxidation of Propane

An ammoxidation of propane was performed in the presence of the oxide catalyst obtained above under the same conditions as in Example 12. The results of the ammoxidation are shown in Table 3.

EXAMPLE 16

Treatment of an Oxide Catalyst with an Aqueous Basic Solution 3.0 g of the oxide catalyst obtained in Example 15 was added to 50.0 g of 10% by weight aqueous ammonia, and then, the resultant suspension was stirred in an atmosphere of air at 25° C. under atmospheric pressure for 6 hours, to thereby obtain a suspension containing a base-treated oxide catalyst. The obtained suspension was subjected to filtration under suction to separate and remove the aqueous ammonia from the base-treated oxide catalyst, so that the base-treated oxide catalyst was recovered from the suspension. After the filtration, the recovered catalyst was washed four times with 50 ml of pure water, and dried in a thermostat set at 200° C. under a stream of air. All of the dried catalyst was charged into a quartz tube having an inner diameter of 20 mm, and then calcined at 550° C. for 2 hours under a stream of nitrogen gas at a flow rate of 500 Nml/min, to thereby obtain a base-treated, calcined oxide catalyst. The nitrogen gas used in the calcination was the same as used in the calcination in Example 12.

Ammoxidation of Propane

An ammoxidation of propane was performed in the presence of the base-treated, calcined oxide catalyst obtained above under the same conditions as in Example 12. The results of the ammoxidation are shown in Table 3.

EXAMPLE 17

Treatment of an Oxide Catalyst with an Aqueous Basic Solution 1.5 g of the oxide catalyst obtained in Example 15 was added to 50.0 g of 2% by weight aqueous ammonia, and then, the resultant suspension was stirred in an atmosphere of air at 25° C. under atmospheric pressure for 6 hours, to thereby obtain a suspension containing a base-treated oxide catalyst. The obtained suspension was subjected to filtration under suction to separate and remove the aqueous ammonia from the base-treated oxide catalyst, so that the base-treated oxide catalyst was recovered from the suspension. After the filtration, the recovered catalyst was washed four times with 50 ml of pure water, and dried in a thermostat set at 200° C. under a stream of air. All of the dried catalyst was charged into a quartz tube having an inner diameter of 20 mm, and then calcined at 550° C. for 2 hours under a stream of nitrogen gas at a flow rate of 350 Nml/min, to thereby obtain a base-treated, calcined oxide catalyst. The nitrogen gas used in the calcination was the same as used in the calcination in Example 12.

Ammoxidation of Propane

An ammoxidation of propane was performed in the presence of the base-treated, calcined oxide catalyst obtained above under the same conditions as in Example 12. The results of the ammoxidation are shown in Table 3.

EXAMPLE 18

Treatment of an Oxide Catalyst with an Aqueous Basic Solution 1.5 g of the base-treated, calcined oxide catalyst obtained in Example 13 was added to 25 g of 5% by weight aqueous ammonia, and the resultant suspension was stirred in an atmosphere of air at 25° C. under atmospheric pressure for 8 hours, to thereby obtain a suspension containing a twice base-treated oxide catalyst. The obtained suspension was subjected to filtration under suction to separate and remove the aqueous ammonia from the twice base-treated oxide catalyst, so that the twice base-treated oxide catalyst was recovered from the suspension. After the filtration, the recovered catalyst was washed four times with 50 ml of pure water, and dried in a thermostat set at 200° C. under a stream of air. All of the dried catalyst was charged into a quartz tube having an inner diameter of 20 mm, and then calcined at 550° C. for 2 hours under a stream of nitrogen gas at a flow rate of 350 Nml/min, to thereby obtain a twice base-treated, calcined oxide catalyst. The nitrogen gas used in the calcination was the same as used in the calcination in Example 12.

Ammoxidation of Propane

An ammoxidation of propane was performed in the presence of the twice base-treated, calcined oxide catalyst obtained above under the same conditions as in Example 12, except that the catalyst weight was changed to 0.1 g, the flow rate (F) of the gaseous feedstock mixture was changed to 12.0 Nml/min and the contact time was changed to 0.58 g·sec/ml. The results of the ammoxidation are shown in Table 3.

TABLE 1

| | Oxidation treatment conditions | | | Results of ammoxidation of propane | | | |
|---|---|---|---|---|---|---|---|
| | Raw material mixture solution temperature (° C.) | Heating and stirring time (hr) | Contact time (g · s/ml) | Conversion of propane (%) | Selectivity for acrylonitrile (%) | Yield of acrylonitrile (%) | Space time yield of acrylonitrile [μmol/{(g · s/ml) · g}] |
| Example 1 | 85 | 4 | 1.17 | 79.3 | 58.7 | 46.6 | 0.374 |
| Example 2 | 100 | 6 | 1.17 | 78.3 | 57.0 | 44.6 | 0.358 |
| Example 3 | 75 | 8 | 1.50 | 86.4 | 50.7 | 43.8 | 0.274 |

TABLE 1-continued

|  | Oxidation treatment conditions | | | Results of ammoxidation of propane | | | |
|---|---|---|---|---|---|---|---|
|  | Raw material mixture solution temperature (° C.) | Heating and stirring time (hr) | Contact time (g · s/ml) | Conversion of propane (%) | Selectivity for acrylonitrile (%) | Yield of acrylonitrile (%) | Space time yield of acrylonitrile [μmol/ {(g · s/ml) · g}] |
| Example 4 | 95 | 10 | 1.17 | 83.4 | 51.9 | 43.5 | 0.349 |
| Example 5 | 150 | 2 | 1.40 | 85.0 | 51.3 | 43.6 | 0.292 |

TABLE 2

|  | Oxidation treatment conditions | | Results of ammoxidation of propane | | | |
|---|---|---|---|---|---|---|
|  | [H$_2$O$_2$:Sb] molar ratio | H$_2$O$_2$-added raw material mixture solution temperature, and stirring time | Contact time (g · s/ml) | Conversion of propane (%) | Selectivity for acrylonitrile (%) | Yield of acrylonitrile (%) | Space time yield of acrylonitrile [μmol/ {(g · s/ml) · g}] |
| Example 6 | 0.12 | 30° C., 30 min | 1.17 | 77.3 | 56.2 | 43.4 | 0.348 |
| Example 7 | 0.52 | 30° C., 1 hr | 1.17 | 78.5 | 55.7 | 43.7 | 0.350 |
| Example 8 | 0.30 | 20° C., 2 hr | 1.17 | 79.9 | 54.6 | 43.6 | 0.350 |
| Example 9 | 0.83 | 25° C., 45 min | 1.17 | 83.2 | 53.9 | 44.8 | 0.359 |
| Example 10 | 2.3 | 30° C., 30 min | 1.29 | 80.4 | 57.2 | 45.9 | 0.373 |
| Example 11 | 0.42 | 30° C., 30 min | 1.67 | 87.1 | 46.8 | 40.8 | 0.226 |
| Comparative Example 1 | 0 | 30° C., 30 min | 2.33 | 70.0 | 30.0 | 21.0 | 0.084 |
| Comparative Example 2 | 0 | 30° C., 40 min | 1.29 | 32.4 | 38.1 | 12.3 | 0.100 |
| Comparative Example 3 | 0 | 30° C., 40 min | 1.67 | 68.0 | 39.7 | 27.0 | 0.150 |

TABLE 3

|  | Aqueous basic solution treatment of catalyst | | | Results of ammoxidation of propane | | | | |
|---|---|---|---|---|---|---|---|---|
|  | Type of aqueous basic solution (concentration) | Treatment conditions | Treatment frequency | Contact time (g · s/ml) | Conversion of propane (%) | Selectivity for acrylonitrile (%) | Yield of acrylonitrile (%) | Space time yield of acrylonitrile [μmol/ {(g · s/ml) · g}] | Ammonia decomposition ratio (%) |
| Example 12 | None | None | None | 1.17 | 73.2 | 58.7 | 46.6 | 0.374 | 45.6 |
| Example 13 | Aqueous ammonia (5 wt %) | 25° C., 8 hr | 1 | 1.17 | 91.5 | 57.2 | 52.3 | 0.420 | 32.1 |
| Example 14 | Aqueous ammonia (5 wt %) | 25° C., 15 hr | 1 | 1.10 | 87.9 | 59.2 | 52.1 | 0.445 | 38.0 |
| Example 15 | None | None | None | 1.17 | 79.1 | 55.5 | 43.9 | 0.304 | 50.2 |
| Example 16 | Aqueous ammonia (10 wt %) | 25° C., 6 hr | 1 | 1.17 | 89.8 | 57.3 | 51.4 | 0.412 | 32.8 |
| Example 17 | Aqueous ammonia (2 wt %) | 25° C., 6 hr | 1 | 1.17 | 91.0 | 56.3 | 51.2 | 0.410 | 33.5 |
| Example 18 | Aqueous ammonia (5 wt %) | 25° C., 8 hr | 2 | 0.58 | 89.3 | 58.5 | 52.2 | 0.729 | 38.4 |

INDUSTRIAL APPLICABILITY

When the oxide catalyst produced by the process of the present invention is used in the production of acrylonitrile or methacrylonitrile, not only is the deterioration of the catalyst suppressed, but also the desired acrylonitrile or methacrylonitrile can be produced in high yield and in high space time yield, so that effective and efficient production of acrylonitrile or methacrylonitrile can be stably performed for a prolonged period of time.

Further, when a base-treated oxide catalyst, which can be obtained by treating the above-mentioned oxide catalyst with an aqueous basic solution, is used, not only can the above-mentioned excellent effects be achieved, but also it becomes possible to suppress the decomposition of ammonia, which is one of the materials for the production of acrylonitrile or methacrylonitrile, into nitrogen, so that the utility of the ammonia can be remarkably enhanced.

What is claimed is:

1. A process for producing an oxide catalyst for use in producing acrylonitrile or methacrylonitrile from propane or isobutane by ammoxidation in the gaseous phase, said oxide catalyst comprising a compound oxide represented by the following formula:

$$Mo_{1.0}V_aSb_bX_cO_n \qquad (I)$$

wherein:

X represents at least one element selected from the group consisting of niobium, tungsten, chromium, titanium, tantalum, zirconium, hafnium, manganese, rhenium, iron, ruthenium, cobalt, rhodium; nickel, palladium, platinum, copper, silver, zinc, boron, gallium, indium, germanium, tin, tellurium, phosphorus, lead, bismuth, rare earth elements, and alkaline earth metals; and a, b, c and n are, respectively, the atomic ratios of vanadium (V), antimony (Sb), X and oxygen (O), relative to molybdenum (Mo), wherein
$0.1 \leq a \leq 1.0$,
$0.01 \leq b \leq 0.6$,
$0 \leq c \leq 1.0$, and n is a number determined by and consistent with the valence requirements of the other elements present in the compound oxide of formula (I), which comprises the following steps (1) to (5):

(1) providing a solution or slurry of a raw material mixture in at least one liquid medium selected from the group consisting of water and an alcohol, said raw material mixture comprising a molybdenum (Mo) compound, a vanadium (V) compound, an antimony (Sb) compound and optionally at least one X compound selected from the group consisting of compounds of elements defined as X in formula (I), (2) subjecting said raw material mixture solution or slurry to at least one oxidation treatment selected from the group consisting of:

(2-a) a heat treatment at 50 to 300° C. in the presence of an oxidizing gas for 1 hour or more, and (2-b) a treatment with an oxidizing liquid, thereby obtaining an oxidized raw material mixture solution or slurry, (3) optionally adding to said oxidized raw material mixture solution or slurry obtained in step (2) at least one X compound selected from the group consisting of compounds of elements defined as X in formula (I), (4) drying said oxidized raw material mixture solution or slurry obtained in step (2) or said oxidized raw material mixture solution or slurry having added thereto said X compound obtained in step (3), to thereby obtain a dried catalyst precursor, and (5) calcining'said dried catalyst precursor to thereby obtain an oxide catalyst comprising a compound oxide of formula (I).

2. The process according to claim 1, wherein said oxidizing gas is at least one member selected from the group consisting of oxygen, air and nitrogen oxides.

3. The process according to claim 1 or 2, wherein said oxidizing liquid is an aqueous solution of at least one oxidizer compound selected from the group consisting of hydrogen peroxide, nitric acid and hypochlorous acid.

4. The process according to claim 3, wherein the amount of said oxidizing liquid is in the range of from 0.01 to 2 in terms of the molar ratio of said at least one oxidizer compound to the antimony contained in said raw material mixture solution or slurry provided in step (1).

5. The process according to claim 3, wherein said oxidizing liquid is an aqueous solution of hydrogen peroxide.

6. The process according to claim 1 or 2, wherein the calcination in step (5) is performed in an inert gas atmosphere which is substantially free from molecular oxygen.

7. The process according to claim 1 or 2, wherein the calcination in step (5) is performed at 400 to 700° C.

8. The process according to claim 1 or 2, which further comprises the steps of (6) contacting said oxide catalyst obtained in step (5) with an aqueous basic solution to obtain a contact mixture containing a base-treated oxide catalyst, and (7) separating and recovering said base-treated oxide catalyst from said contact mixture.

9. The process according to claim 8, wherein said aqueous basic solution is an aqueous solution of at least one compound selected from the group consisting of ammonia, an alkali metal hydroxide, an alkaline earth metal hydroxide, an alkali metal carbonate, an alkaline earth metal carbonate, an alkali metal salt of an organic acid, an alkaline earth metal salt of an organic acid and an amine.

10. The process according to claim 9, wherein said aqueous basic solution is an aqueous solution of ammonia.

11. The process according to claim 8, which further comprises the step (8) of calcining said base-treated oxide catalyst recovered in step (7) from said contact mixture.

12. The process according to claim 11, wherein the calcination in step (8) is performed in an inert gas atmosphere which is substantially free from molecular oxygen.

13. The process according to claim 11, wherein the calcination in step (8) is performed at 400 to 700° C.

14. A process for producing acrylonitrile or methacrylonitrile, which comprises reacting propane or isobutane with ammonia and molecular oxygen in the gaseous phase in the presence of the oxide catalyst produced by the process of claim 1.

* * * * *